(12) United States Patent
Maitra et al.

(10) Patent No.: US 6,555,376 B2
(45) Date of Patent: Apr. 29, 2003

(54) PROCESS OF ENTRAPPING GENETIC MATERIALS IN ULTRA-LOW SIZE NANOPARTICLES OF INORGANIC COMPOUNDS TO FORM NON-VIRAL CARRIERS

(75) Inventors: Amarnath Maitra, Delhi (IN); Subho Mozumdar, New Delhi (IN); Susmita Mitra, Delhi (IN); Indrajit Roy, Delhi (IN)

(73) Assignee: University of Delhi, Department of Chemistry, Delhi (IN)

( * ) Notice: Subject to any disclaimer, the term of this patent is extended or adjusted under 35 U.S.C. 154(b) by 0 days.

(21) Appl. No.: 10/201,247

(22) Filed: Jul. 24, 2002

(65) Prior Publication Data

US 2003/0027336 A1 Feb. 6, 2003

(30) Foreign Application Priority Data

Aug. 1, 2001 (IN) ............................................. 823/2001

(51) Int. Cl.[7] .............................................. C12N 15/88
(52) U.S. Cl. ...................................... 435/458; 536/23.1
(58) Field of Search .......................... 435/458; 536/23.1

(56) References Cited

U.S. PATENT DOCUMENTS 5,266,205 A * 11/1993 Fulton et al.
6,355,271 B1 * 3/2002 Bell et al.

* cited by examiner

*Primary Examiner*—James Ketter
(74) *Attorney, Agent, or Firm*—Sidley Austin Brown & Wood LLP (57) ABSTRACT

The present invention relates to a process of entrapping genetic materials in nanoparticles of inorganic metal salts of size below 100 nm diameter to form non-viral carriers for delivery of genes. The process comprises the steps of dissolving surfactants and a cosurfactant in oil to obtain reverse micelles. An aqueous solution of genetic material is added to the reverse micelles. Thereafter the reverse micelles are divided into two equal parts. To one part, aqueous solution of inorganic metal salts is dissolved to obtain optically clear and transparent reverse micelles. To the second part aqueous solution of precipitating agent is added to obtain optically clear and transparent reverse micelles. The two equally divided parts of reverse micelles are mixed to form inorganic nanopartcles encapsulating added genetic material. Thereafter, the nanoparticles are separated from reverse micelles, the inorganic nanoparticles are dispersed in water and dialyzed to remove free metal salts, surfactant and oil.

17 Claims, 6 Drawing Sheets

PROCESS OF ENTRAPPING GENETIC MATERIALS IN ULTRA-LOW SIZE NANOPARTICLES OF INORGANIC COMPOUNDS TO FORM NON-VIRAL CARRIERS

FIELD OF THE INVENTION

This invention relates to a process of entrapping genetic materials in nanoparticles of inorganic compounds of size below 100 nm diameter to form non-viral carriers suitable for delivery of genes including those of therapeutic interest in appropriate cells.

BACKGROUND OF THE INVENTION

As it is known, the ability to safely and efficiently transfer foreign DNA into cells is a fundamental goal in biotechnology. In recent years, with the advent of recombinant DNA technology, a surge in research activity has occurred in the field of DNA transfer across cell lines. This activity, which has taken the shape of what is popularly known as gene therapy, is a medical/surgical intervention technique which is being developed as a 'molecular medicine' and requires genes to be introduced into cells in order to treat a wide variety of till now incurable human diseases. Potential applications are numerous, given the diversity of the genes to be used as well as the possible target cells.

Today's gene therapy research may be seen as pursuing intelligent drug design through a logical extension of results of fundamental biomedical research on the molecular basis of disease. The term gene therapy applies to approaches to disease treatment based on the insertion of genetic material (DNA and RNA) into a cell's genetic pool either to correct an underlying defect or to modify the characteristics of a cell via expression of the newly inserted gene. In order to successfully implement this technique, effective means of delivering the therapeutic gene to the target cell is required, in such a way that the gene can be expressed at the appropriate level and for a sufficient duration. Two broad approaches have been used to deliver DNA and RNA to cells, namely viral and non-viral vectors, which have different advantages as regards efficiency, ease of production and safety. One of the most powerful methods for gene-transfer is the use of viral vectors. A viral vector is genetically engineered from 'wild-type' virus, and consists of a modified viral genome and virion structure. By retaining the protein coat of the original virus, the vector is able to bind and penetrate the cell more effectively while protecting the genome from endogenous enzymes. As for the original viral genome (wild-type), only the essential viral sequence necessary for transcription is retained. There are a number of viral vectors that are currently being used for transfecting cells. Of interest are retroviruses (enveloped single strand RNA), adenoviruses (non-enveloped double stranded DNA) and adeno-associated viruses (linear single stranded DNA). Due to their inherent nature of penetrating and inserting their genetic material (genome) into the target cell, viral vectors result in very high transfection rates. In addition to escaping the target cell's endonucleases, viral genes also possess promoters and enhancers that increase the probability of genetic expression.

Although viral vectors are attractive in terms of the scientific strategy of exploiting natural mechanism, there are some major drawbacks associated with them. They suffer from inherent difficulties of effective pharmaceutical processing, immunogenicity, difficulty in targeting to specific cell types, scale up and the possibility of reversion of an engineered virus to the wild type The safety risks include 'Insertional Mutagenesis' and toxicity problems. Ever since the death of Jesse Gelsinger in September 2000, scientists have began to severely question the safety aspects related to viral vector mediated gene delivery. Consequently, a major focus is now being given at the development and use of alternative vectors based on synthetic, non-viral systems for safe and efficient gene delivery.

The problems associated with viral vectors have led to a growing interest in non-viral gene delivery systems. Non-viral vectors are techniques of introducing a coding DNA sequence without the means of a virus. The self-assembly of artificial plasmid (pDNA) containing vectors is required for the development of such vectors. These methods of gene transfer require only a small number of gene, have a virtually infinite capacity, have no infectious or mutagenic capability and large scale production is possible using pharmaceutical techniques. DNA itself is negatively charged, as is the cell membrane and therefore the entry of naked DNA is restricted due to electrical repulsion forces. To reduce this repulsion, many researchers have encased the polynucleotide with a cationic membrane so as to alter the electrical distribution and charge of the complex. These include lipid-based carriers, polycationic lipids, polylysine, polyornithine, histones and other chromosomal proteins, hydrogel polymers and precipitated calcium phosphate (CaPi). One of the major drawbacks of the use of these non-viral vectors is their low transfection efficiency which is caused due to exposure of DNA in the hostile DNAse environment due to simple electrostatic compaction of DNA with the polymeric materials. Among these, the technique of calcium phosphate co-precipitation for in vitro transfection is used as a routine laboratory procedure. This procedure involves a reaction of calcium chloride with sodium phosphate to form a water insoluble calcium phosphate precipitate, which can bind to pDNA. This method heavily relies on the fact that divalent metal cations, such as $Ca^{2+}$, $Mg^{2+}$, $Mn^{2+}$ and $Ba^{2+}$ can form ionic complexes with the helical phosphates of DNA. Calcium phosphate, therefore, forms complexes with the nucleic acid backbone and thus may impart a stabilizing function to certain DNA structures. When added to a cell monolayer, the cells take up the water insoluble calcium phosphate-pDNA complex (Ca Pi-pDNA) by transportation across the membrane through $Ca^{2+}$ ion mediated channel formation. This process is an example of ion channel mediated endocytosis. Once inside the cell, the CaPi-pDNA complex is broken down inside the endosome, thereby releasing the pDNA into the cytosol, which, under suitable circumstances, can be incorporated into the host cell genome. In addition, being inorganic particles, calcium phosphate is highly stable, non-toxic, non-antigenic and non-carcinogenic.

Although extremely safe, the major shortcoming of this process is the poor transfection efficiency as compared to that of viral vectors. The general belief is that the transfection with CaPi-DNA is a low efficiency procedure partly because most of the endocytosed DNA is quickly degraded and excreted to the cytosol. A small fraction of the remaining DNA macromolecules important for gene transfer may be delivered from the endosomal compartment through membrane bound organelles to the nucleus without traversing the cytosol. Moreover, although calcium phosphate precipitation method is simple, effective and still widely used in laboratory for in vitro transfection, the method is hampered by the difficulty of applying to in vivo studies, especially delivery of DNA to any particular cell types. Due to bulk precipitation of calcium phosphate, the method also suffers from variation in calcium phosphate-DNA particle size, which causes variation among experiments.

Process for production of inorganic nanoparticles has been described in U.S. Pat. Nos. 5,460,831 and 5,879,715. Although the process has described the method of preparation of particles of size as small as 10 nm diameter the preparative method does not describe anything about the encapsulation of biologically active materials inside the matrices of these nanoparticles. Calcium Phosphate nanoparticles of size 300 nm and above have been reported in U.S. Pat. No. 6,355,271, which have been, used as carriers and as controlled release matrices for biologically active materials. Virus-like-size particles i.e. particles of size below 100 nm diameter encapsulating genetic materials, which are biologically safe and cost effective, are the main criteria of a non-viral vector for effective delivery of genes. We have described in this invention of the preparation of below 100 nm diameter inorganic nanoparticles doped with genetic material such as DNA or RNA as a non-viral carrier for the delivery of genes or their modified compounds.

OBJECTS AND SUMMARY OF THE INVENTION

The object of this invention is to propose a novel process for the preparation of nearly monodispersed non-toxic and biocompatible inorganic materials such as calcium, magnesium, manganous phosphates and the like, encapsulating genetic materials such as DNA and RNA and having a size maximum upto 100 nm diameter with near monodispersity.

Another object of this invention is to propose a process for the preparation of nearly monodispersed inorganic nanoparticles of subcolloidal size with targeted DNA and RNA materials. Yet another object of this invention is to propose a process for the preparation of nearly monodispersed inorganic nanoparticles dispersed in aqueous buffer and free from any toxic materials.

Further object of this invention is to propose a process for the complete encapsulation of the therapeutic genetic material into the matrix of the inorganic nanoparticles to secure them from outer intervention in vivo or cell culture in vitro till they are exposed to the target site within the cell.

A still further object of this invention is to propose a process for the preparation of nearly monodispersed DNA or RNA loaded inorganic nanoparticles covered with strongly adhesive and non-toxic biocompatible polymeric material chemically conjugated with targetable ligand so that the particles can be targeted to specific cell types in vivo, which obviates the disadvantages associated with these of the prior art.

To achieve these objectives, this invention provides a process of entrapping genetic materials in nanoparticles of inorganic compounds of size below 100 nm diameter to form non-viral carriers suitable for delivery of genes including those of therapeutic interest comprising the steps of:

(a) dissolving 0.01M to 1.0M of a surfactant or a mixture of surfactant and a cosurfactant in oil to obtain reverse micelles, (b) adding an aqueous solution of genetic material to the reverse micelles, (c) dividing the reverse micelles obtained in step (b) into two equal parts, (d) dissolving aqueous solution of 0.1 to 1.0M inorganic metal salts in one part of reverse micelles (step c) to obtain optically clear and transparent reverse micelles after dissolution, (e) adding aqueous solution of 0.1 to 1.0M precipitating agent in the second part of reverse micelles (step c) to obtain optically clear and transparent reverse micelles after dissolution, (f) maintaining the same molar ratio of water to surfactant in steps d and e, (g) mixing the reverse micelles of both steps (d) and (e) and stirring to form inorganic nanoparticles encapsulating added genetic material, (h) separating the nanoparticles from reverse micelles, and (i) dispersing the inorganic nanoparticles in water and dialyzing to remove free metal salts, surfactant and oil.

The above process further comprises coating the nanoparticles surface by adhesive polymeric compound and chemically conjugating ligand molecules for targeting the nanoparticels to specific cell type.

The surfactant is selected from the group containing anionic, cationic and non-ionic type.

The oil used for the preparation of reverse micelles is hydrocarbon oil.

The hydrocarbon oil is a saturated long chain or branched chain hydrocarbon of $C_6$ to $C_{10}$ chain length.

The hydrocarbon oil is n-Hexane.

The reverse micelles contain a long chain alcohol from butanol to octanol in the form of cosurfactant when it is required to stabilize the reverse micelles.

The genetic materials are selected from DNA and RNA and genetic modifications thereof.

The inorganic metal salts are selected from the group containing calcium chloride, magnesium sulphate and manganous sulphate and the precipitating agent is disodium hydrogen phosphate.

The inorganic metal salt is ferric chloride and the precipitating agent is ammonium hydroxide. The separation of nanoparticle is carried out by precipitating with ethanol and ishing the precipitate with ethanol.

The inorganic nanoparticles are calcium phosphate, magnesium phosphate, manganous phosphate and ferric oxide.

The nanoparticles after separating from micelles be dispersed in water either by mild agitating, prolonged stirring or by sonication.

The molar ratio of water to surfactant ($W_0$) is in the range of $W_0=10$ to $W_0=40$.

The nanaoparticles encapsulating genetic material have diameter in the range of 10 nm to 100 nm.

The adhesive polymeric materials used for coating the nanoparticles is polyacrylic acid.

The ligand is a molecule having at least one amino group selected from the group containing sugar, an antibody, folic acid, transferrin and biotine or derivatives thereof The carboxylic group of polyacrylic acid is conjugated with the amino group of the ligand molecule.

In accordance with this invention the aqueous core of a reverse micellar droplet is used as a nanoreactor for the preparation of nanoparticles. Near monodispersity of the inorganic particles is possible because reverse micellar droplets in which the precipitation reactions are carried out are highly monodispersed. The size of the nanoparticles is governed by the size of the aqueous core of reverse micellar droplets, which is dependent on the molar ratio of water to surfactant (wo) of the reverse micelles. The wo of reverse micelles is kept in the range of 10 to 40 and the nanoparticles formed in such reverse micelles have average size below 100 nm diameter.

The composition of aqueous phase of reverse micellar droplets is regulated in such a manner so as to keep the entire mixture in an optically transparent reverse micellar phase. The range of aqueous phase can not be defined apriori as this would depend on factors such as nature and solubility of the metal salt used the nature and solubility of the precipitating agent and their interaction with the polar head group of the surfactant. The only factor that is important is that the system should be in an optically transparent reverse micellar phase.

In accordance with the present invention the nanoparticles have size range of upto 100 nm diameter. In accordance with this invention the aqueous core of a reverse micellar droplet having a predetermined wo value is effectively used as nanoreactor to prepare ultrafine nanoparticles and to encapsulate the plasmid DNA, RNA or their derivatives. The process of the present invention has achieved extremely small size nanoparticles (diameter in the range of 10 nm to 100 nm) of greater uniformity.

The strategy involves precipitation of insoluble inorganic metal salts in the form of nanoparticles encapsulating DNA and RNA in the aqueous core of the reverse micellar droplets. As the aqueous core of reverse micelles are of nanosized dimensions, the particles prepared inside them are also nanometer sized. In addition, the aqueous core of reverse micelles has long been known as a medium for solubilizing biomolecules like enzymes, antibodies, other proteins, nucleic acids etc., without damaging their biological activities. In this work, we have achieved inorganic materials to undergo precipitation reaction inside the aqueous core of reverse micelles and have obtained nearly monodispersed nanoparticles completely encapsulating (more than 99%) genetic materials. We have also demonstrated that these nanoparticles doped with genetic material can be used as efficient non-viral vectors for delivery of genes in vitro and in vivo. Because of the extremely low size of the particles, their aqueous dispersion will have easy circulation in the blood. Additionally, these nanoparticles could also be targeted using ligands to receptors of specific cell types in vivo. For this we could cover the surface of these inorganic nanoparticles by some adhesive polymer having a suitable functional group, which can be chemically conjugated with appropriate ligand molecules. Through our invention we have overcome the two major impediments for using inorganic materials as non-viral vectors: (i) use of ultrafine nanoparticles so that the aqueous dispersion of these inorganic salts can become easily injectable systems and (ii) targeting these nanoparticles to specific cell types by coating the nanoparticle surface with adhesive polymer and conjugating them with appropriate ligand. By this way, inorganic nanoparticles mediated gene delivery can become more advantageous compared to other viral and non-viral carriers in the sense that the method is absolutely safe as well as cost effective. With the prospect of reviving this methodology of using calcium phosphate as carriers by improving on the preparative conditions, we have tried to devise a strategy that would make the process more efficient and useful, as well as suitable for in vivo applications.

BRIEF DESCRIPTION OF THE DRAWINGS

The invention will now be described with reference to the accompanying drawings and forgoing examples.

DETAILED DESCRIPTION

Figure 1:
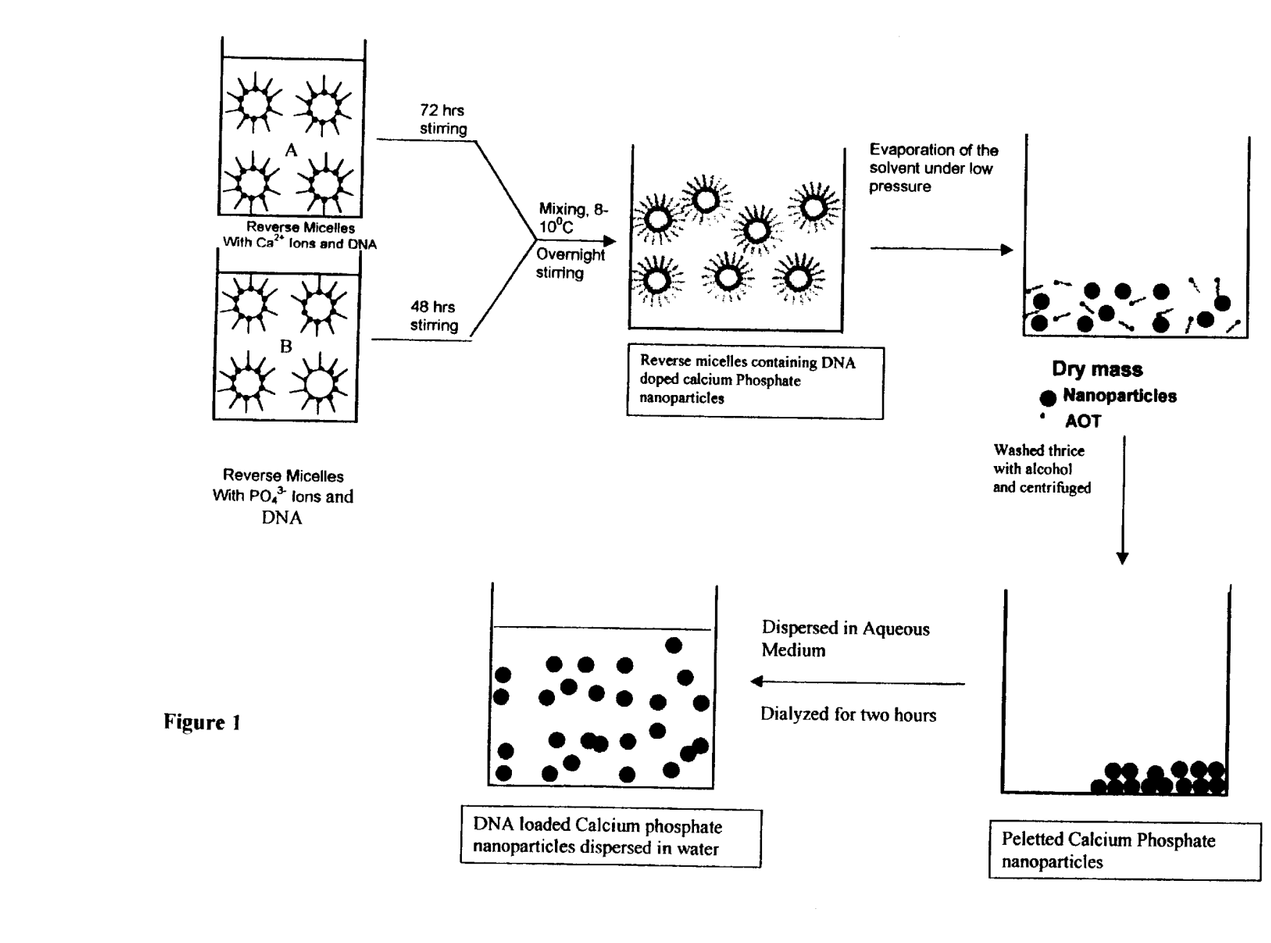
FIG. 1 shows a flow diagram for the preparation of inorganic nanoparticles in reverse micelles.

Reference is now made to FIG. 1 of the accompanying drawings, which illustrates the flow diagram for the preparation of inorganic nanoparticles using reverse micelles. Inorganic nanoparticles are prepared in the aqueous core of reverse micellar droplets as follows: When using AOT/water/n-Hexane reverse micelles, 0.1M sodium bis (ethylhexyl)sulphosuccinate (AOT) in hexane solution is prepared In 0.1M AOT in hexane, aqueous solution of metal salt, double distilled water and the genetic material to be encapsulated are dissolved by continuous stirring to form reverse micelles A. In another AOT in hexane, aqueous solution of precipitating agent e.g. $Na_2HPO_4$, to precipitate metal phosphates or ammonium hydroxide to precipitate metal oxides, double distilled water, 0.2M Tris-HCl buffer of required pH in which the precipitation of metal salt would have taken place and the genetic material to be encapsulated, is dissolved by continuous stirring to form reverse micelles B. Both the reverse micelles have same molar ratio of water to surfactant i.e. wo and are optically clear solutions. Then, reverse micelles B is slowly added to reverse micelles A at the rate of 5 mL per hour with continuous stirring at 8–10° C. The solution is then, further stirred in cold for some time. The resulting solution is translucent due to solid inorganic nanoparticles dispersed in the reverse micelles. Next, to separate the nanoparticles, the solution is centrifuged at 8000 rpm. Alternatively, after evaporation of the solvent, it can be treated with dry ethanol to precipitate nanoparticles. The nanoparticles (containing the entrapped genetic material) are settled at the bottom of the tube, and the supernatant solution is drained off The pelleted nanoparticles are washed with hexane or ethanol three times to remove any residual surfactant. Finally, the nanoparticles are redispersed in 10 mL of double distilled water by mild agitation, stirring or sonication. The aqueous dispersed nanoparticles are dialysed in a 12 kD cut-off cellulose membrane whereby residual small molecules like surfactant, hexane, unentrapped DNA or RNA are separated leaving behind highly purified nanoparticles doped with added genes dispersed in water. This aqueous dispersion of nanoparticles is lyophilized to fine powder for further use.

The potential use of these inorganic nanoparticles have been explored as vectors for hepatic gene transfer. Nanoparticles are incubated with a highly adhesive polymer like polyacrylic acid (PAA), followed by dialysis to remove excess polymer. The PAA molecules adhered on the surface of the calcium phosphate nanoparticles are further modified by conjugating the carboxylic groups with p-aminophenyl-1-thio-β-D-galactopyranoside (PAG) using 1-ethyl-3-(3-dimethylaminopropyl)-carbodiimide hydrochloride (EDCI). The galactopyranoside moiety serves as a surface ligand for recognizing asialoglycoprotein receptor on liver cells. The tagged nanoparticles shows preferential expression in liver tissue relative to lung, spleen and muscle. These observations suggest redistribution of genetic material in relation to the particle surface characteristics.

EXAMPLES

The following examples are given by way of illustration of the present invention and should not be construed to limit the scope of present invention.

Example-1

Preparation of Calcium Phosphate Nanoparticles Encapsulating pSVβgal

Calcium phosphate nanoparticles are prepared in the aqueous core of AOT/Hexane reverse micellar droplets as follows: 0.1M sodium bis(ethylhexyl)sulphosuccinate (AOT) in hexane solution is prepared. In 25 mL of 0.1M AOT in hexane, 50 μL of aqueous solution of $CaCl_2$ (1.3M), 390 μL double distilled water and 10 μL of pDNA (400 ug/mL) are dissolved by continuous stirring for 72 hours to form reverse micelles A. In another 25 ml of AOT in hexane, 50 μL of aqueous solution of $Na_2HPO_4$ (5% w/v), 340 μL of double distilled water, 50 μL of 0.2M Tris-HCl buffer (pH 6) and 10 μL of pDNA (400 μg/mL) are dissolved by continuous stirring for 48 hours to form reverse micelles B. Both the reverse micelles A and B have wo=10 and are optically clear solutions. Then, reverse micelle B is slowly added to reverse micelles A at the rate of 5 mL per hour with continuous stirring at 8–10° C. The solution is, then, further stirred in cold for another 6 hours. The resulting solution is translucent due to calcium phosphate nanoparticles dispersed in the reverse micelles.

Example-2

Calcium phosphate nanoparticles are prepared in the aqueous core of CTAB/n-Butanol/n-Octane reverse micellar droplets as follows: 0.1M of CTAB mixed with n-Butanol in the molar ratio 1:0.73 in n-Octane solution is prepared. In 25 mL of 0.1M reverse micelles, 50 μL of aqueous solution of $CaCl_2$(1.3M), 390 μL double distilled water and 10 μL of pDNA (400 ug/mL) are dissolved by continuous stirring for 72 hours to form reverse micelles A. In another 25 ml of CTAB/n-Butanol/n-Octane reverse micelles of same composition as reverse micelles A, 50 μL of aqueous solution of $Na_2HPO_4$ (5% w/v), 340 μL of double distilled water, 50 μL of 0.2M Tris-HCl buffer (pH 6) and 10 μL of pDNA (400 μg/mL) are dissolved by continuous stirring for 48 hours to form reverse micelles B. Both the reverse micelles A and B have wo=10 and are optically clear solutions. Then, reverse micelle B is slowly added to reverse micelles A at the rate of 5 mL per hour with continuous stirring at 8–10° C. Then, reverse micelle B is slowly added to reverse micelles A at the rate of 5 mL per hour with continuous stirring at 8–10° C. The solution is, then, further stirred in cold for another 6 hours. The resulting solution is translucent due to calcium phosphate nanoparticles dispersed in the reverse micelles.

Example-3

Separation of Nanoparticles from Reverse Micelles and Redispersion in Water

Next, to separate the nanoparticles, the reverse micelle solution is centrifuged at $8\times10^3$ rpm for half an hour. The nanoparticles (containing the entrapped DNA) settle at the bottom of the centrifuge tube, and the supernatant solution is drained off. The pelleted nanoparticles are washed with hexane three times to remove any residual surfactant. Finally, the nanoparticles are redispersed in 10 mL of double distilled water by sonication in cold for two hours. The aqueous dispersed nanoparticles are dialysed for 10 hours in a 12 kD cut-off cellulose membrane whereby residual small molecules like surfactant, hexane, unentrapped DNA etc. are separated leaving behind highly purified calcium phosphate nanoparticles doped with pDNA dispersed in water.

Example-4

Separation of Nanoparticles from Reverse Micelles and Redispersion in Water

Alternatively, the nanoparticles doped with genetic materials can also be separated by the following method. The hydrocarbon solvent of the reverse micelles is removed using rotary vacuum evaporator. The mass left in the flask is treated with 10 ml of dry ethanol and it is vortexed for 30 minutes. The ethanolic solution is kept at 4° C. for 12 hours when the nanoparticles are settled at the bottom of the flask and the supernatant alcoholic solution is pipetted out. The nanoparticles are then washed thrice each time with 10 ml dry ethanol and is separated by centrifugation at 3000 rpm for 10 minutes. The residue left after centrifugation is then dispersed in 10 ml sterile water and dialyzed for 2 hours to get a transluscent dispersed system of loaded nanoparticles in water.

Example-5

Preparation of pUC19 Entrapped Manganous Phosphate Nanoparticles

The method of preparation is same as above (in Example 1). In 25 ml of 0.1M AOT in hexane, 70 ul of 1M Manganous sulphate, 360 μl of double distilled water and 20 μl of pUC19 DNA (150 ug/ml) are dissolved. In another set of 25 ml of reverse micelles, 70 μl of 5%w/v disodium hydrogen phosphate, 310 μl of double distilled water, 20 ul of pUC19 (150 ug/ml) and 50 μl of ammonium hydroxide+ammonium chloride buffer (pH=10) are added The two reverse micelles are mixed together and stirred as mentioned in example 1. The nanoparticles are separated by using dry ethanol and washed and dried for further use following the procedure as shown in example 4.

Example-6

Size and Shape of These Nanoparticles Using QELS and TEM

Figure 2A:
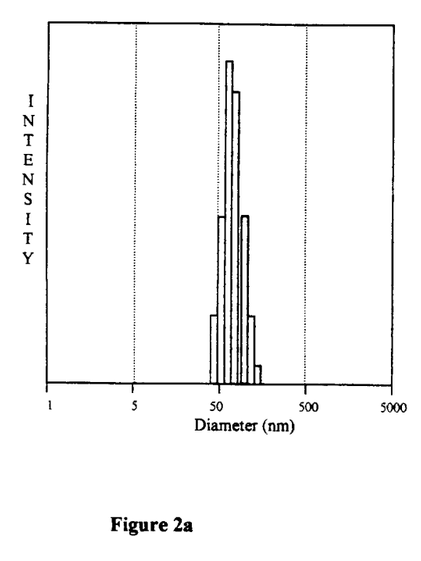
FIG. 2a shows a QELS diagrams of the size of the particle.

The size of the particles obtained is determined using quasi elastic light scattering (QELS) measurements. 10 mg of lyophilized powder is redispersed in 10 ml water and the aqueous solution is filtered through 0.2 um Millipore filter. 3 ml of such solution is used for size determination. BI8000 Brookhaven light scattering instrument is used and the intensity of scattered light at 90° is analyzed through Brookhaven autocorrelator. The size and size distribution of the nanoparticles are calculated from Stoke Einstein equation. The particles are reasonably monodisperse with size around 80 nm in diameter (FIG. 2a). The sizes of the nanoparticles are influenced by wo as well as reaction temperature, concentration of calcium ions and speed of mixing of the two reverse micellar systems.

Figure 2B:
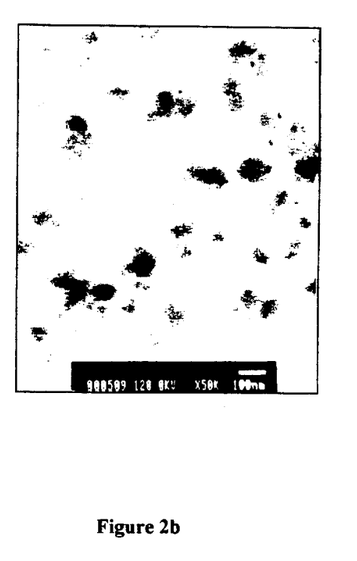
FIG. 2b shows TEM picture of the nanoparticles.

Transmission Electron Micrograph (TEM) shows that the particles are more or less spherical in shape having solid core with rough surface texture (FIG. 2b).

Example-7

Agarose Gel Electrophoresis Studies

Figure 3:
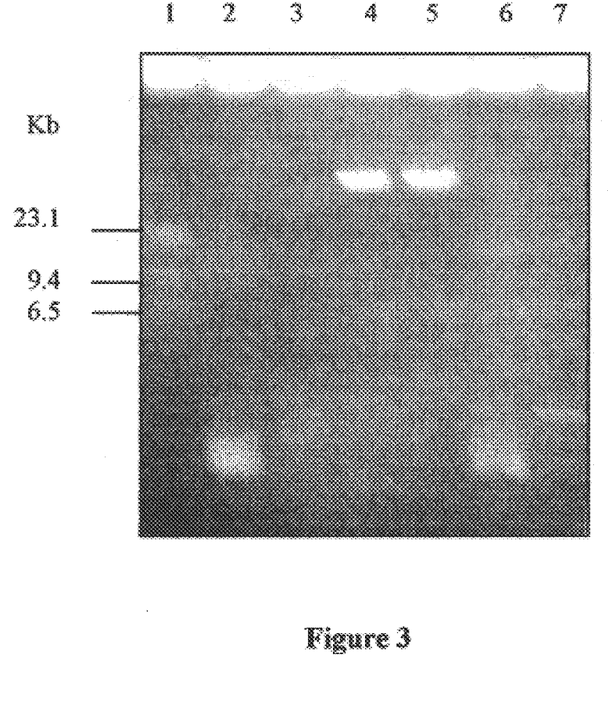
FIG. 3 shows gel electrophoresis of DNA free and encapsulated.

We have subjected the DNA doped inorganic nanoparticles to extensive DNaseI treatment followed by electrophoresis on 1% agarose gel (FIG. 3). We have found that while free plasmid DNA (pUC19) moves at its usual position in the gel, pUC19 encapsulated in the matrix of the nanoparticle is right at the top of the gel and hardly moved This is a positive indication that the DNA has been encapsulated by the nanoparticle matrix. Moreover, while free pUC19 is completely digested by DNAseI (5 mg/ml) treatment for half an hour, encapsulated pUC19 is totally protected against similar DNAseI digestion As expected, this is quite contrary to the plasmid DNA adsorbed on the surface of the nanoparticles. In this case, we find that the level of protection offered to the DNA is extremely low and the DNA is highly prone to nearly total degradation by DnaseI.

FIG. 3 shows Agarose Gel electrophoresis of free, entrapped and adsorbed pUC19 DNA in different lanes.

Lane #1: Molecular Weight marker
Lane #2: Free pUC19 DNA
Lane #3: Free pUC19 DNA treated with DNaseI
Lane #4: pUC19 DNA entrapped in Calcium phosphate nanoparticles
Lane #5: pUC19 DNA entrapped in Calcium phosphate nanoparticles and treated with DNaseI
Lane #6: pUC19 DNA adsorbed on Calcium phosphate nanoparticles
Lane #7: pUC19 DNA adsorbed on Calcium phosphate nanoparticles and treated with DNaseI Example-8

Invitro Transfection Studies in Mammalian Cell Lines Using DNA Doped Nanoparticles Use of calcium phosphate nanoparticles encapsulating DNA has been observed to achieve the benefit of nanoparticle mediated gene transfer by co-delivery of calcium ions when these DNA doped nanoparticles are added to Jurkat cell line in vitro. The data is furnished in FIG. 4. The plasmid DNA used in this case is pSVβgal, which carries the reporter gene coding for the enzyme β-galactosidase. Therefore, the transfection efficiency can be determined by measuring the activity of β-galactosidase in the individual in vitro systems. As observed from the data given in the figure, the transfection efficiency, measured as the activity of the enzyme β-galactosidase, obtained using these nanoparticles is nearly comparable to that obtained using a commercially available transfecting reagent (Superfect, obtained from Promega, USA) and is significantly higher than that obtained using calcium phosphate DNA co-precipitate.

Figure 4:
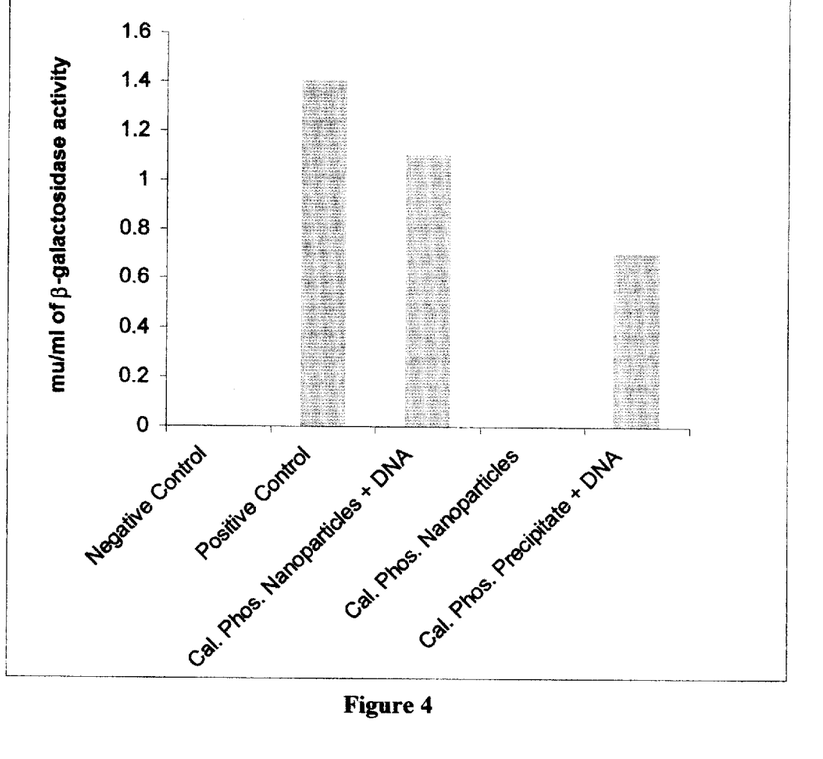
FIG. 4 shows in vitro transfection of pSVβgal in Jurkat cell lines.

FIG. 4 shows In vitro transfection efficiency of DNA doped calcium phosphate nanoparticles in Jurkat cell line. The positive control is the commercially available transfecting agent (Superfect).

Example-9

Invivo Transfection Experiment: Biodistribution Studies

Figure 5A:
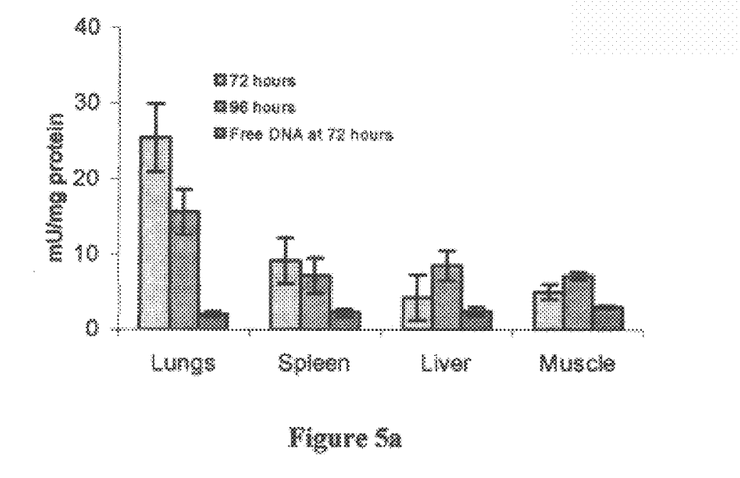
FIG. 5a shows in vivo biodistribution of pSVβgal loaded calcium phosphate nanoparticles administered through intramuscular route.
Figure 5B:
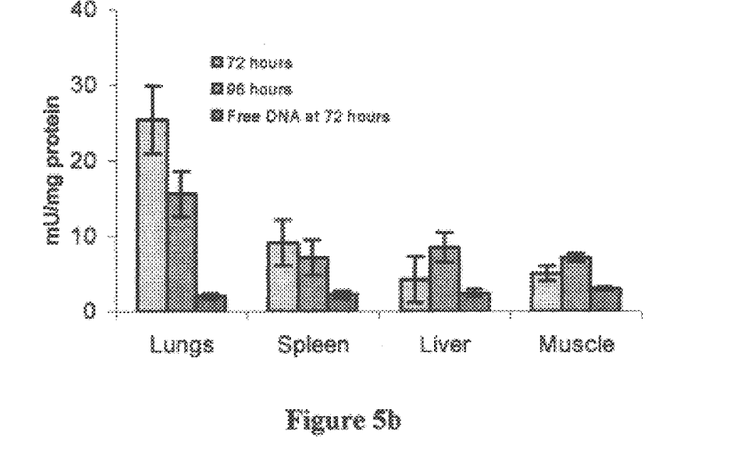
FIG. 5b shows in vivo bio distribution of pSVβgal loaded calcium phosphate nanoparticles administered through interaperitoneal route.

To assess the potential utility of calcium phosphate nanoparticle mediated gene delivery in the animal, in general, and to a specific organ of the animal, in particular, we have used the murine model. Experiments have been conducted on young Swiss albino mice, and we have studied the local gene expression, as well as expression in different body tissues. Interestingly, both intramuscular (i.m.) and intraperitoneal (i.p.) administration of encapsulated pSVβgal have resulted in expression of the β-galactosidase enzyme in major organs of the body (FIGS. 5a &b). Local expression is observed in the tibialis muscle bundle. The enzyme activity detected is over and above that of the background endogenous activity. Free DNA expression is negligible compared to that of the nanoparticles.

Figure 6A:
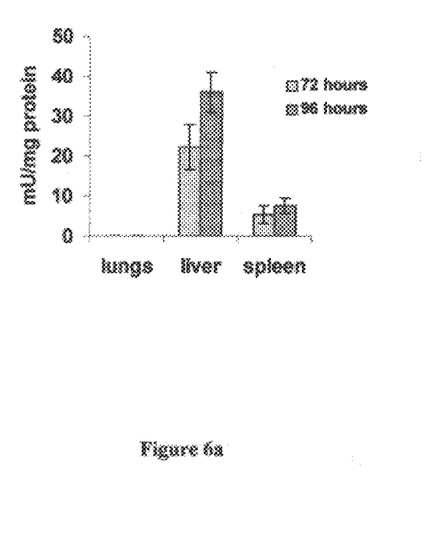
FIG. 6a shows β-galactosidase expression in vivo after administration of a galactopyranoside taged Calcium phosphate nanoparticles encapsulating pSVβgal through ip injections.

FIG. 6a shows transfection efficiency as measured by β-galactosidase expression in different body tissues after in vivo administration of pSVβGal plasmid DNA encapsulated in calcium phosphate nanoparticles in young in swiss albino mice (15 g) are injected intraperitoneally.

Figure 6B:
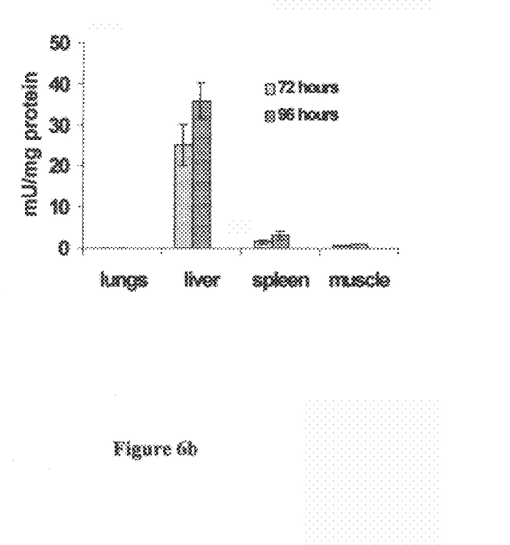
FIG. 6b shows β-galactosidase expression in vivo after administration of galactopyranoside taged Calcium Phosphat nanoparticles encapsulating pSVβgal through im injections.

FIG. 6b shows the transfection efficiency as measured by β-galactosidase expression in different body tissues after in vivo administration of pSVβGal plasmid DNA encapsulated in calcium phosphate nanoparticles. Free plasmid DNA is injected into the tibialis muscle bundle of mice Example-10

In Vivo Transfection Studies Using Surface Modified Calcium Phosphate Nanoparticles for Targeted Delivery of DNA to Liver Specific Cells.

The liver is an important target for gene therapy, because of its large size and protein synthetic capacity. Moreover, there is a need to target genes transfer to the liver for treatment of diseases involving defects in members of segmental enzymatic pathways that are unique to the organ. Models for hepatic gene delivery have been developed using viral vectors, virosomes and other non-viral vectors, but all of these methods have important limitations. In our studies we have explored the potential use of calcium phosphate nanoparticles as vectors for hepatic gene transfer. Nanoparticles are incubated with a highly adhesive polymer like polyacrylic acid (PAA), followed by dialysis to remove excess polymer. The PAA molecules which adhered on the surface of the calcium phosphate nanoparticles are further modified by conjugating the carboxylic groups with p-aminophenyl-1-thio-D-galactopyranoside (PAG) using 1-ethyl-3-(3-dimethylaminopropyl)-carbodiimide hydrochloride EDCI). The galactopyranoside moiety serves as a surface ligand for recognizing asialoglycoprotein receptor on liver cells. The tagged nanoparticles show preferential expression in liver tissue relative to lung, spleen and muscle. These observations suggest redistribution of genetic material in relation to the particle surface characteristics.

That which is claimed is:

1. A process of entrapping genetic materials in nanoparticles of inorganic metal salts of size below 100 nm diameter to form non-viral carriers for delivery of genes comprising the steps of:

(a) dissolving 0.01M to 1.0M of a surfactant or a mixture of surfactant and a cosurfactant in oil to obtain reverse micelles, (b) adding an aqueous solution of genetic material to the reverse micelles, (c) dividing the reverse micelles obtained in step (b) into two equal parts, (d) dissolving aqueous solution of 0.1 to 1.0M inorganic metal salts in one part of reverse micelles (step c) to obtain optically clear and transparent reverse micelles after dissolution, (e) adding aqueous solution of 0.1 to 1.0M precipitating agent in the second part of reverse micelles (step c) to obtain optically clear and transparent reverse micelles after dissolution, (f) maintaining the same molar ratio of water to surfactant in steps d and e, (g) mixing the reverse micelles of both steps (d) and (e) and stirring to form inorganic nanoparticles encapsulating added genetic material, (h) separating the nanoparticles from reverse micelles, and (i) dispersing the inorganic nanoparticles in water and dialyzing to remove free metal salts, surfactant and oil.

2. A process as claimed in claim 1 further comprising coating the nanoparticles surface by adhesive polymeric compound and chemically conjugating ligand molecules for targeting the nanoparticles to specific cell type.

3. A process as claimed in claim 1 wherein the surfactant is selected from anionic, cationic and non-ionic type.

4. A process as claimed in claim 1 wherein the oil used for the preparation of reverse micelles is hydrocarbon oil.

5. A process as claimed in claim 4 wherein the hydrocarbon oil is a saturated long chain or branched chain hydrocarbon of $C_6$ to $C_{10}$ chain length.

6. A process as claimed in claim 5 wherein the hydrocarbon oil is n-Hexane.

7. A process as claimed in claim 1 wherein the cosurfactant is a long chain alcohol from butanol to octanol for stabilizing the reverse micelles.

8. A process as claimed in claim 1 wherein the genetic materials are selected from DNA and RNA.

9. A process as claimed in claim 1 wherein the inorganic metal salts are selected from calcium chloride, magnesium sulphate and manganous sulphate and the precipitating agent is disodium hydrogen phosphate.

10. A process as claimed in claim 1 wherein the inorganic metal salt is ferric chloride and the precipitating agent is ammonium hydroxide.

11. A process as claimed in claim 1 wherein the separation of nanoparticle is carried out by centrifugation or by precipitating with ethanol and washing the precipitate with ethanol.

12. A process as claimed in claim 1 wherein the inorganic nanoparticles are calcium phosphate, magnesium phosphate, manganous phosphate and ferric oxide.

13. A process as claimed in claim 1 wherein the inorganic nanoparticles after separating from micelles be dispersed in water either by mild agitating, prolonged stirring or by sonication.

14. A process as claimed in claim 1 wherein the molar ratio of water to surfactant ($W_0$) in both parts of reverse micelles is equal and is in the range of $W_0=10$ to $W_0=40$.

15. A process as claimed in claim 1 wherein the inorganic nanoparticles encapsulating genetic material have diameter in the range of 10 nm to 100 nm.

16. A process as claimed in claim 2 wherein the adhesive polymeric materials used for coating the nanoparticles is polyacrylic acid having carboxylic group and the ligand is a molecule having at least one amino group selected from sugar, an antibody, folic acid, trasferrin and biotine or derivatives thereof.

17. A process as claimed in claim 16 wherein the carboxylic group of polyacrylic acid is conjugated with the amino group of the ligand molecule.

* * * * *